United States Patent

Hori et al.

[11] Patent Number: 5,183,824
[45] Date of Patent: Feb. 2, 1993

[54] AZOLE DERIVATIVES AND ANTIFUNGAL DRUGS CONTAINING THE SAME AS AN ACTIVE COMPONENT

[75] Inventors: Kimihiko Hori; Akira Sakaguchi, both of Utsunomiya; Koichi Ishida, Tochigi; Tomoko Nomura, Utsunomiya; Keiko Suzuki, Utsunomiya; Shuichi Tsuchiya, Utsunomiya, all of Japan

[73] Assignee: Kao Corporation, Tokyo, Japan

[21] Appl. No.: 829,507

[22] Filed: Feb. 3, 1992

Related U.S. Application Data

[62] Division of Ser. No. 609,777, Nov. 7, 1990, Pat. No. 5,110,826.

[30] Foreign Application Priority Data

Nov. 9, 1989 [JP] Japan .................................. 1-290031
Feb. 6, 1990 [JP] Japan .................................. 2-25155

[51] Int. Cl.$^5$ ................. A01N 43/653; C07D 249/08
[52] U.S. Cl. ................................ 514/383; 548/267.2; 548/267.4; 548/267.8
[58] Field of Search ...................... 514/383; 548/267.2, 548/267.4, 267.8

[56] References Cited

U.S. PATENT DOCUMENTS 5,051,439 9/1991 Schermanz et al. ................. 514/383

Primary Examiner—Patricia L. Morris
Attorney, Agent, or Firm—Oblon, Spivak, McClelland, Maier & Neustadt

[57] ABSTRACT

An azole derivative represented by the following formula (I):

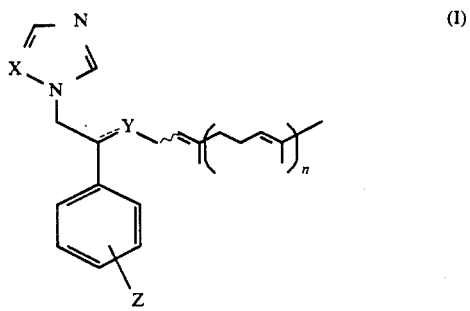

wherein X is a nitrogen atom or CH, Y is an oxygen atom, a sulfur atom, an imino group, a methylimino group or a group represented by $=N-O-$, Z is one or two halogen atoms, n stands for a number of 1 or 2, the wavy line means that stereochemistry of the double bond is either E or Z; or an acid adduct thereof.

They exhibit strong antifungal activities and are very useful in the therapy for fungus diseases.

Also disclosed is an antifungal drug containing said compound as an active ingredient.

2 Claims, No Drawings

AZOLE DERIVATIVES AND ANTIFUNGAL DRUGS CONTAINING THE SAME AS AN ACTIVE COMPONENT

This is a division, of application Ser. No. 07/609,777, filed on Nov. 7, 1990, now U.S. Pat. No. 5,110,826, issued on May 5, 1992.

BACKGROUND OF THE INVENTION

1) Field of the Invention:

This invention relates to novel azole derivatives having strong antifungal activities and antifungal drugs containing the same as an active component.

2) Description of the Background Art:

Some azole derivatives are known to have antifungal activities, which include clotrimazole, miconazole, sulconazole, ketoconazole, fluconazole and the like.

In the treatment of fungus diseases, medicines should desirably have possibly broadest antifungal spectra and should act not only topically but also systemically, in view that fungi which normally don't cause infections are sometimes responsible for mycoses as observed in the superinfection or the opportunistic infections, and that serious deep-seated mycoses are sometimes caused.

Development of novel medicines capable of overcoming the resistance against conventional chemotherapeutic drugs has still been demanded.

Under such circumstances, the present investors have undertaken extensive studies and have found that novel compounds represented by the following formula (I) exhibited strong antifungal activities and useful for the therapy of fungus diseases. This finding has led to the completion of this invention.

SUMMARY OF THE INVENTION

Accordingly, a primary object of the present invention is to provide an azole derivative represented by the following formula (I):

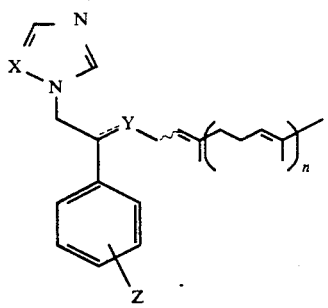

wherein X is a nitrogen atom or CH, Y is an oxygen atom, a sulfur atom, an imino group, a methylimino group or a group represented by $=N-O-$, Z is a hydrogen atom, one or two halogen atoms, a nitro group or a trifluoromethyl group, n stands for a number of 1 or 2, the wavy line means that stereochemistry of the double bond is of either E or Z; or an acid adduct thereof.

A further object of the invention is to provide an antifungal drug containing the same as an active component.

DETAILED DESCRIPTION OF THE INVENTION AND PREFERRED EMBODIMENTS

The compounds of formula (I) can be prepared, for example, by the reaction of compound (III) with alkenyl halide (II) in the absence or the presence of a base according to the following reaction scheme:

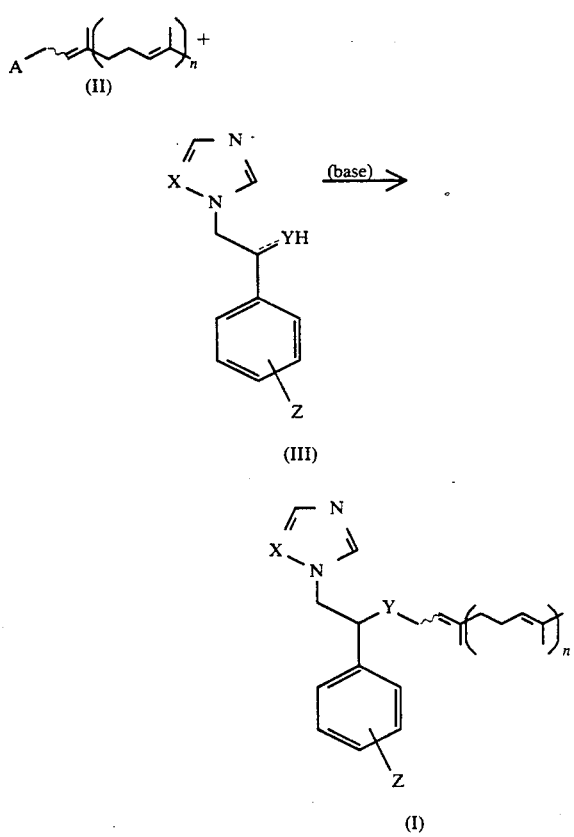

wherein X, Y, Z and n have the same meanings as defined before, and A is a halogen atom.

The reaction for the preparation of compound (I) may be carried out using 1.0 to 3.0 moles of compound (II) based on 1 mole of compound (III) at $-10°$ C. to 200° C., preferably 30° C. to 100° C., with stirring for several hours. Any bases may be used so far as they don't inhibit the reaction. Preferable examples of the base are sodium hydride, sodium amide, potassium carbonate, sodium carbonate, potassium hydroxide and sodium hydroxide. Any solvents may be used so far as they are inert to the reaction. Preferable examples of the solvent are N,N-dimethylformamide, dimethylsulfoxide, ethylene glycol diethylether, tetrahydrofuran, ethanol and methanol. After the reaction is completed, the solvent is evaporated and the target compound is isolated by column chromatography or the like.

Another method may be given for the preparation of the compound of formula (Ia) which has a sulfur atom at Y of formula (I), where a halide (IV) reacts with mercaptan (V) in the absence or the presence of a base according to the following reaction scheme:

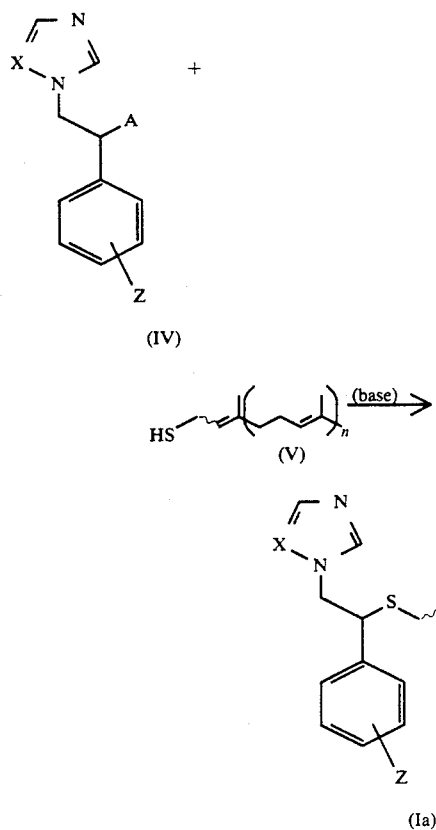

wherein X, Z, n and A have the same meanings as defined before.

This reaction may be carried out using 1.0 to 2.0 moles of compound (V) based on 1 mole of compound (IV) at −10° C. to 100° C., preferably 30° C. to 70° C., with stirring for several hours. Any bases may be used so far as they don't inhibit the reaction. Preferable examples of the base are sodium hydride, sodium amide, potassium carbonate, sodium carbonate, potassium hydroxide and sodium hydroxide. Any solvents may be used so far as they are inert to the reaction. Preferable examples of the solvent are N,N-dimethylformamide, ethanol and methanol. After the reaction is completed, the solvent is evaporated and the target compound (Ia) is isolated by column chromatography or the like.

The thus obtained compounds (I) of the present invention can be converted into acid adducts as needed through any conventional method. Examples of such acid adducts are inorganic acid adducts such as nitrate, hydrochloride and the like; and organic acid adducts such as fumarate, maleate, tartarate, citrate and the like.

Hereinafter are presented test results of compound (I) of the present invention in terms of pharmaceutical actions and acute toxicity.

(1) Antifungal activities (in vitro):

A plate of a series of diluted specimen was prepared under steriled conditions using Sabouraud's agar medium (glucose 2%, peptone 1%, agar 1.5%), to which 1 μl of each of the test fungus solutions was inoculated by using a quantitative platinum loop. Trichophyton sp. which belongs to the dermatophytes and Candida sp. which belongs to the yeast were cultured at 27° C. and 37° C., respectively, and their growthes were evaluated seven days after and two days after respectively to obtain minimum growth-inhibitory concentrations (MIC). The results are shown in Table 1.

TABLE 1

| Compound Nos. | MIC (μg/ml) Strains | |
|---|---|---|
| | Trichophyton sp. | Candida sp. |
| 1 | 5~10 | 40 |
| 2 | 40~80 | >80 |
| 3 | 0.16~5.0 | 20~40 |
| 4 | 1.25~20 | 20 |
| 5 | 5.0 | 20 |
| 6 | 5~10 | 20~40 |
| 7 | >80 | >80 |
| 8 | 10~20 | 40 |
| 9 | 10~20 | 40 |
| 10 | 20 | >80 |
| 11 | 5~20 | 40 |

(2) Inhibitory action against ergosterol biosynthesis:

Inhibitory action against ergosterol biosynthesis, which is one of the characteristic actions of azole antifungal drugs, was evaluated.

*T. mentagrophytes* (TIMM 1189) and *C. albicans* (TIMM 0144) were used in the test as representatives of the dermatophytes and yeast, respectively. Microconidia of *T. mentagrophytes* (TIMM 1189) were collected by way of gauze filtration and cultured in a Sabouraud glucose liquid medium at a concentration of $1 \times 10^6$/ml at 27° C. until no increase was observed. Concerning *C. albicans* (TIMM 0144), fresh cultures were prepared and cultured in GPY broth at a concentration of $1 \times 10^6$/ml at 37° C. until they reached the logarithmic growth phase. *T. mentagrophytes* (TIMM 1189) and *C. albicans* (TIMM 0144) were allowed to intake [$^{14}$C] sodium acetate over 2 hours in the presence of a test compound at concentrations of $10^{-1}$ to $10^{-6}$ μg/ml and $10^{-1}$ to $10^{-4}$ μg/ml, respectively, and sterols were measured by TLC. Inhibitory action against C-14 demethylation depending on cytochrome P450 was obtained.

The results are shown in Table 2.

TABLE 2

| Compounds Nos. | ED$_{50}$ (g/ml) Strains | |
|---|---|---|
| | T. mentagraphytes (TIMM 1189) | C. albicans (TIMM 0144) |
| 1 | $1.0 \times 10^{-5}$ | $6.9 \times 10^{-3}$ |
| 2 | $4.2 \times 10^{-2}$ | $4.7 \times 10^{-2}$ |
| 6 | — | $4.0 \times 10^{-2}$ |
| 8 | — | $9.7 \times 10^{-3}$ |
| 9 | — | $7.2 \times 10^{-2}$ |
| 10 | — | $5.2 \times 10^{-2}$ |

(3) Direct cell-membrane damaging:

Direct cell-membrane damaging, which is one of the characteristic actions of azole antifungal drugs, was evaluated.

As a test strain, *C. albicans* (TIMM 0144) was used. Fresh cultures of *C. albicans* (TIMM 0144) were washed to make a deionized aqueous solution containing the same at a concentration of $1 \times 10^8$/ml. In the presence of a test compound at a concentration of 40 μg/ml, potassium ion leakage concentration was measured 15 minutes after by way of atomic absorption spectrometry to evaluate the direct cell-membrane damaging. The results are shown in Table 3.

TABLE 3

| Compound Nos. | Potassium ion leakage rate (%) |
| --- | --- |
| 1 | 81 |
| 2 | 55 |
| 6 | 74 |
| 8 | 65 |
| 10 | 47 |

(4) Antifungal activities (in vivo):

Hartley white female guinea pigs were used in this test. The back hair were depilated to form a round area having a diameter of 2 cm. $1 \times 10^8$ microconidia of *T. mentagrophytes* (TIMM 1189) were inoculated therein for infection. From the fifth day of the inoculation, a composition containing 1% test compound (base: white petrolatum) was applied once a day for 6 consecutive days. Thereafter, the animals were left for 1 day, and slaughtered while removing the blood. The suffered skin was taken, cut and subjected to the retro-culture. The negative ratio of the strain was measured. The results are shown in Table 4.

TABLE 4

| Compound Nos. | Negative ratio (%) |
| --- | --- |
| 1 | 95 |
| 6 | 89 |
| 8 | 46 |
| 9 | 34 |
| 10 | 37 |
| Clotrimazole | 24 |
| Miconazole | 27 |

(5) Acute Toxicity:

Compound (I) of the present invention, which was obtained in Example 1 described hereinafter, was found to have a $LD_{50}$ value of 1000 mg/kg or more when dosed orally on mice.

As described above, compounds (I) of the present invention or acid adducts thereof have excellent antifungal activities and high safety. These compounds can be formulated to antifungal drugs solely or in combination with a conventional base and other active ingredients. Thus formulated antifungal drugs according to the present invention can be administered orally, externally, by injection or in any other forms. The dose may be controlled depending on the age, weight, symptom or the like. In case of oral administration, preferable amount on the basis of compound (I) is 100 to 3000 mg, more preferably 200 to 1400 mg for an adult, and in case of intravenous-injection, 50 to 1000 mg, more preferably 100 to 300 mg for an adult. Compounds (I) of the present invention can be formed into tablets, granules, powders, capsules, suspensions, injections, supositories, external applications or the like for the therapy of fungus diseases.

Summing up the effects of the invention compounds, it is noted that azole derivatives (I) of the present invention have strong activities in terms of ergosterol biosynthesis inhibition and direct cell-membrane damaging. Their toxicity is very low, and $LD_{50}$ values when dosed orally on mice are all 1000 mg/kg or more. Thus, it is concluded that the compounds (I) of the present invention are very useful as an antifungal drug for fungus diseases of animals including the human. They are especially useful for treating topical mycoses caused by Candida, Trichophyton, Microsporum, or Epidermophyton, and mucous infections such as thrush or the vaginal candida caused by *Candida albicans*. Moreover, they are useful for treating systemic mycoses caused by *Candida albicans*, *Cryptococcus neoformans*, *Aspergillus flavus*, *Aspergillus fumigatus*, Coccidioides, Paracoccidioides, Histoplasma or Blastomyces.

EXAMPLES

The present invention will hereinafter be described in further detail by the following Examples. It should however be borne in mind that the present invention is not necessarily be limited thereto.

EXAMPLE 1

Preparation of 1-[2-(2,4-dichlorophenyl)-2-((E)-3,7-dimethylocta-2,6-dienyloxy)ethyl]-1H-imidazole (Compound 1)

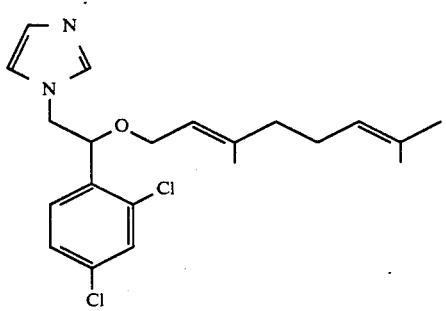

To a stirred solution of 1-(2,4-dichlorophenyl)-2-(1H-imidazole-1-yl)ethanol (2.06 g=8.0 mmol) in dimethylformamide (25 ml) was gradually added sodium hydride (0.48 g=12.0 mmol) at room temperature. The reaction mixture was stirred at 40° C. for 30 minutes. And to the stirred reaction mixture was added (E)-3,7-dimethylocta-2,6-dienyl-1-bromide (2.60 g=12.0 mmol) in dimethylformamide and the reaction mixture was stirred for 15 minutes at 80° C. After evaporation of the solvent under reduced pressure, the residue was diluted with chloroform. The chloroform layer was washed with water and dried over anhydrous sodium sulfate. Concentration followed by column chromatography on silica gel (chloroform:methanol=100:1~75:1) gave 1.46 g of Compound 1 as a colorless oil.

$^1$H-NMR(CDCl$_3$) δ ppm: 1.50(s,3H), 1.60(s,3H), 1.69(s,3H), 1.87~2.22(m,4H), 3.79(dd,1H,J=7.3, 11.7 Hz), 3.91(dd,1H,J=6.6, 11.7 Hz), 3.99(dd,1H,J=7.3, 14.3 Hz), 4.15(dd,1H,J=2.7, 14.3 Hz), 4.92(dd,1H,J=2.7, 7.3 Hz), 5.03~5.12(m,1H), 5.17~5.24(m,1H), 6.93(s,1H), 7.02(s,1H), 7.22~7.38(m,2H), 7.38~7.43(m,1H), 7.48(s,1H).

IR $\nu^{neat}$cm$^{-1}$: 2868, 2932, 2860, 1590, 1506, 1473, 1440, 1386, 1287, 1233, 1218, 1107, 1095, 1077, 1044, 1005, 909, 867, 825, 789, 756, 663, 627

The obtained oil was dissolved in a proper amount of ethanol, and added 0.43 g of fumaric acid in ethanol. After removal of the ethanol, a small amount of ether and then hexane were added to give white crystals. The crystals were collected by filtration and recrystallized from isopropylether-hexane. 0.97 g of fumarate of Compound 1 was obtained as white crystals.

EXAMPLE 2

Preparation of
1-[2-(2,4-dichlorophenyl)-2-((E,E)-3,7,11-trimethyl-dodeca-2,6,10-trienyloxy)ethyl]-1H-imidazole (Compound 2)

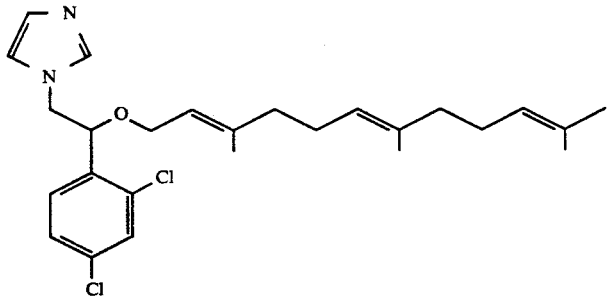

Procedures of Example 1 were followed, and a colorless oil was obtained.

$^1$H-NMR(CDCl$_3$) δ ppm: 1.50 (s, 3H), 1.60 (s, 6H), 1.68 (s, 3H), 1.84~2.22 (m, 8H), 3.78 (dd, 1H, J=7.5, 11.6 Hz), 3.90 (dd, 1H, J=6.5, 11.6 Hz), 3.98 (dd, 1H, J=7.3, 14.4 Hz), 4.16 (dd, 1H, J=2.8, 14.4 Hz), 4.91 (dd, 1H, J=2.8, 7.3 Hz), 5.01~5.29 (m, 3H), 6.93 (s, 1H), 7.02 (s, 1H), 7.26~7.32 (m, 2H), 7.38~7.42 (m, 1H), 7.45 (s, 1H).

IR $\nu^{neat}$cm$^{-1}$: 2928, 2860, 1592, 1506, 1472, 1442, 1386, 1232, 1108, 1092, 1044, 824, 790, 662

Procedures of Example 1 were followed, and white crystals of fumarate of Compound 2 were obtained.

EXAMPLE 3

Preparation of
1-[2-((E)-3,7-dimethylocta-2,6-dienyloxy)-2-(2-nitrophenyl)ethyl]-1H-imadazole (Compound 3)

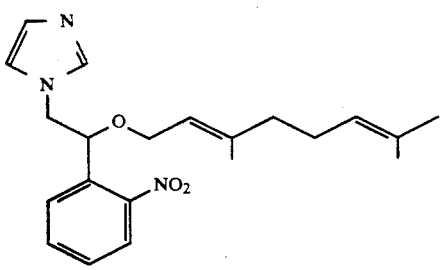

Procedures of Example 1 were followed using 2-(1H)-imidazole-1-yl)-1-(2-nitrophenyl)ethanol as a starting material, and a light-yellow oil was obtained.

$^1$H NMR (CDCl$_3$ δ ppm) 1.43(s,3H),1.60(s,3H),1.68(s,3H),1.90~2.14(m,4H). 3.72(dd,1H,J=11.6,7.5 Hz),3.84(dd,1H,J=11.6,7.5 Hz), 4.09(dd,1H,J=14.2,7.4 Hz),4.37(dd,1H,J=14.2,2.2 Hz), 5.00~5.19(m,3H),7.04(s,2H),7.45~7.58(m,2H)7.65(s,1H), 7.67(s,1H),8.06(t,1H,J=8.1 Hz)

IR $\nu^{neat}$cm$^{-1}$: 2936, 2860, 1528, 1446, 1348, 1288, 1232, 1098, 1076, 1032, 1002, 818, 790, 752, 726, 662.

Procedures of Example 1 were followed, and fumarate of Compound 3 was obtained as light-yellow crystals.

EXAMPLE 4

Preparation of
1-[2-((E)-3,7-dimethylocta-2,6-dienyloxy)-2-(2-trifluoromethylphenyl)ethyl]-1H-imidazole (Compound 4)

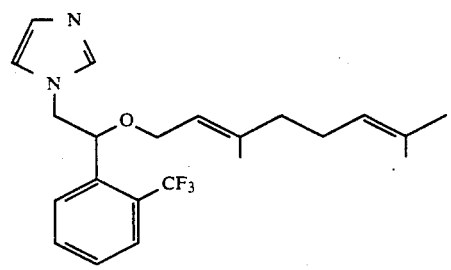

Procedures of Example 1 were followed using 2-(1H-imidazole-1-yl)-1-(2-trifluoromethylphenyl)ethanol as a starting material, and a colorless oil was obtained.

$^1$H NMR (CDCl$_3$ δ ppm): 1.46(s,3H),1.60(s,3H),1.68(s,3H),1.83~2.15(m,4H), 3.75(dd,1H,J=11.6,7.5 Hz),3.85(dd,1H,J=11.6,6.4 Hz), 3.99(dd,1H,J=14.5,7.6 Hz),4.11(dd,1H,J=14.5,2.5 Hz), 4.86~4.99(m,1H),5.00~5.10(m,1H),5.16(t,1H,J=6.8 Hz), 6.96(s,1H),7.04(s,1H), 7.40~7.75(m,5H)

IR $\nu^{neat}$cm$^{-1}$: 2972, 2932, 2864, 1506, 1456, 1380, 1316, 1288, 1264, 1232, 1164, 1122, 1076, 1056, 1034, 662, 774.

Procedures of Example 1 were followed, and fumarate of Compound 4 was obtained as white crystals.

EXAMPLE 5

Preparation of
1-[2-((E)-3,7-dimethylocta-2,6-dienyloxy)-2-phenylethyl]-1H-imidazole (Compound 5)

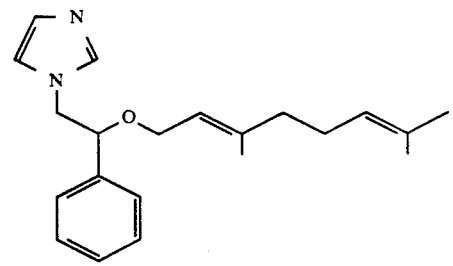

Procedures of Example 1 were followed using 2-(1H-imidazole-1-yl)-1-phenylethanol as a starting material, and a colorless oil was obtained.

¹H NMR (CDCl₃ δ ppm): 1.48(s,3H),1.60(s,3H),1.69(s,3H),1.96~2.20(m,4H), 3.77(dd,1H,J=11.6,7.4 Hz),3.91(dd,1H,J=11.6,6.4 Hz), 4.05(dd,1H,J=14.2,4.5 Hz),4.14(dd,1H,J=14.2,7.2 Hz), 4.49(dd,1H,J=7.2,4.5 Hz),5.01~5.18(m,1H), 5.24(t,1H,J=6.4 Hz),6.89(s,1H),7.00(s,1H), 7.20~7.38(m,5H),7.40(s,1H).

IR $\nu^{neat}$cm⁻¹: 3032, 2972, 2928, 2860, 1670, 1506, 1456, 1382, 1286, 1232, 1106, 1074, 1028, 906, 816, 760, 724, 700, 662, 630.

Procedures of Example 1 were followed, and fumarate of Compound 5 was obtained as white crystals.

EXAMPLE 6

Preparation of
1-[2-(2,4-dichlorophenyl)-2-((Z)-3,7-dimethylocta-2,6-dienyloxy)ethyl]-1H-imidazole (Compound 6)

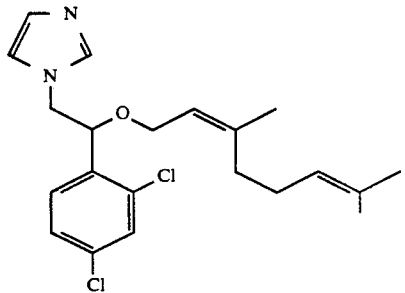

Procedures of Example 1 were followed, and a colorless oil was obtained.

¹H-NMR(CDCl₃) δ ppm: 1.52(s,3H), 1.64(s,3H), 1.71(s,3H), 1.82~2.10(m,4H), 3.76(dd,1H,J=7.3,11.4 Hz), 3.89(dd,1H,J=6.6,11.4 Hz), 4.00(dd,1H,J=7.3,14.4 Hz), 4.17(dd,1H,J=2.9,14.4 Hz), 4.91(dd,1H,J=2.9,7.3 Hz), 4.98(m,1H), 5.20(dd,1H,J=6.6,7.3 Hz), 6.93(s,1H), 7.01(s,1H), 7.20~7.39(m,2H), 7.41(d,1H,J=1.7 Hz), 7.45(s,1H).

IR $\nu^{neat}$cm⁻¹: 2968, 2926, 2860, 1590, 1566, 1506, 1473, 1449, 1383, 1287, 1233, 1107, 1095, 1077, 1044, 1008, 867, 825, 789, 735, 663, 627.

Procedures of Example 1 were followed, and white crystals of fumarate of Compound 6 were obtained.

EXAMPLE 7

Preparation of
1-[2-(4-bromophenyl)-2-((E)-3,7-dimethylocta-2,6-dienyloxy)ethyl]-1H-triazole (Compound 7)

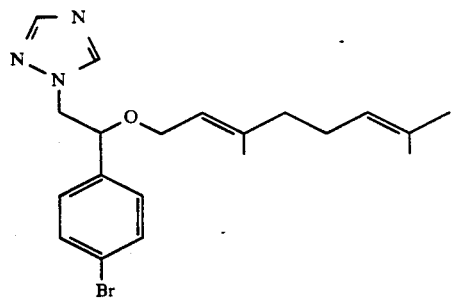

To a stirred solution of 1-(4-bromophenyl)-2-(1H-triazole-1-yl)ethanol (1.00 g=3.7 mmol) in dimethylformamide (10 ml) was gradually added sodium hydride (0.16 g=4.1 mmol) at room temperature. The reaction mixture was stirred at room temperature for 90 minutes. And to the stirred reaction mixture was added (E)-3,7-dimethylocta-2,6-dienyl-1-bromide (0.82 ml=4.1 mmol) in dimethylformamide. Stirring was continued for 60 minutes at room temperature. After evaporation of the solvent under reduced pressure, the residue was diluted with ethyl acetate, washed with water, followed by drying over anhydrous sodium sulfate. Concentration followed by column chromatography on Silica gel (ethyl acetatehexane=3:1) gave 1.12 g of Compound 4 as a colorless oil.

¹H-NMR(CDCl₃) δ ppm: 1.46(s,3H), 1.60(s,3H), 1.68(s,3H), 1.84~2.13(m,4H), 3.73(dd, 1H,J=7.5,11.6 Hz), 3.88(dd,1H,J=6.4,11.6 Hz), 4.27(dd,1H,J=5.2,14.0 Hz), 4.30(dd,1H,J=7.4,14.0 Hz), 4.66(dd,1H,J=5.2,7.4 Hz), 4.97~5.19(m,2H), 7.20(d,2H,J=8.3 Hz), 7.52(d,2H,J=8.3 Hz), 7.95(s,1H), 8.11(s,1H).

IR $\nu^{neat}$cm⁻¹: 2928, 1506, 1490, 1450, 1276, 1140, 1072, 1012, 824, 680.

The thus obtained oil was dissolved in a proper amount of ethanol, and added fumaric acid (0.47 g ) in ethanol. After removal of the ethanol, the residue was recrystallized from acetone-hexane. 0.52 g of fumarate of Compound 4 was obtained as white crystals.

EXAMPLE 8

Preparation of
1-[2-(2,4-dichlorophenyl)-2-((E)-3,7-dimethylocta-2,6-dienylamino)ethyl]-1H-imidazole (Compound 8):

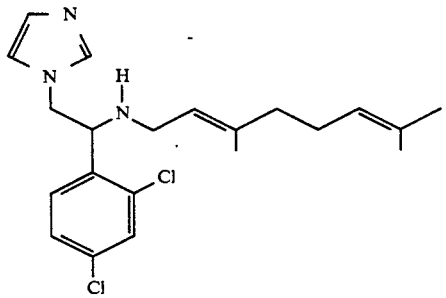

To a stirred solution of 1-(2,4-dichlorophenyl)-2-(1H-imidazole-1-yl)ethylamine (2.50 g=9.8 mmol) in dimethylformamide (30 ml) was added potassium carbonate (1.35 g=9.8 mmol) and (E)-3,7-dimethylocta-2,6-dienyl-1-bromide(1.94 ml=9.8 mmol) at room temperature. Stirring was continued for 30 minutes at room temperature. After evaporation of the solvent under reduced pressure, the residue was diluted with ethyl acetate, washed with water, followed by drying over anhydrous sodium sulfate. Concentration followed by column chromatography on silica gel (chloroform:methanol=150:1) gave 1.08 g of Compound 8 as a colorless oil.

¹H-NMR(CDCl₃) δ ppm: 1.25(s,1H), 1.44(s,3H), 1.60(s,3H), 1.68(s,3H), 1.73~2.17(m,4H), 2.99(dd,1H,J=7.5, 13.6 Hz), 3.04(dd, 1H, J=6.6, 13.6 Hz), 3.97(dd, 1H, J=7.7, 14.0 Hz), 4.18(dd, 1H, J=4.2, 14.0 Hz), 4.51(dd, 1H, J=4.2, 7.7 Hz), 4.98~5.15(m,2H), 6.87(s, 1H), 7.04(s, 1H), 7.23~7.45(m, 4H).

IR $\nu^{neat}$cm⁻¹: 2968, 2928, 2856, 1590, 1506, 1470, 1440, 1386, 1284, 1232, 1108, 1078, 1046, 1032, 864, 824, 788, 754, 662.

The thus obtained oil was dissolved in a proper amount of ethanol, and added fumaric acid (1.08 g) in ethanol. The residue was recrystallized from acetone-hexane. 0.89 g of fumarate of Compound 8 was obtained as white crystals.

EXAMPLE 9

Preparation of 1-[2-(2,4-dichlorophenyl)-2-{N-((E)-3,7-dimethylocta-2,6-dienyl)-N-methylamino}ethyl]-1H-imidazole (Compound 9)

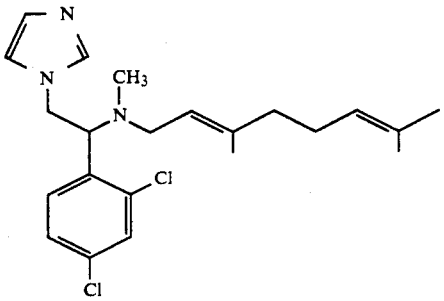

Procedures of Example 8 were followed, and a colorless oil was obtained.

$^1$H-NMR(CDCl$_3$) δ ppm: 1.52(s, 3H), 1.60(s, 3H), 1.68(s, 3H), 1.89~2.20(m, 4H), 2.31(s, 3H), 3.02 (d, 2H,J=6.8 Hz), 4.12~4.40(m, 3H), 5.03~5.12(m, 1H), 5.12~5.23(m, 1H), 6.70(s, 1H), 6.92(s, 1H), 7.14~7.25(m, 3H), 7.33(d, 1H,J=1.6 Hz).

IR $\nu^{neat}$cm$^{-1}$: 2972, 2924, 2860, 1590, 1508, 1472, 1454, 1386, 1234, 1108, 1080, 1050, 822, 664.

Procedures of Example 8 were followed, and fumarate of Compound 9 was obtained as white crystals.

EXAMPLE 10

Preparation of 1-[2-(2,4-dichlorophenyl)-2-((E)-3,7-dimethylocta-2,6-dienylthio)ethyl]-1H-imidazole (Compound 10)

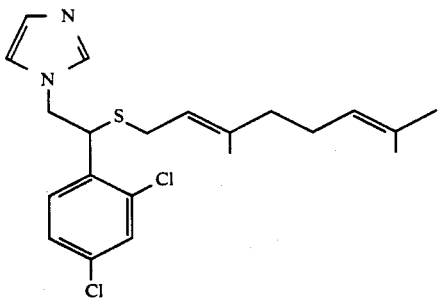

To a stirred solution of (E)-3,7-dimethylocta-2,6-dienylmercaptan (1.00 g=5.9 mmol) in methanol (40 ) was added potassium hydroxide (0.33 g=5.8 mmol) and 1-chloro-1-(2,4-dichlorophenyl)-2-(1H-imidazole-1-yl)ethane (1.62 g=5.9 mmol) in ethanol at room temperature, and then the reaction mixture was refluxed for 90 minutes. After cooling, the methanol was evaporated, and then the residue was diluted with chloroform. The chloroform layer was washed with water, followed by drying over anhydrous sodium sulfate. Concentration followed by column chromatography on silica gel (ethyl acetate:hexane=2:3) gave 1.32 g of Compound 10 as a colorless oil.

$^1$H-NMR(CDCl$_3$) δ ppm: 1.46(s, 3H), 1.59(s, 3H), 1.67(s, 3H), 1.90~2.17(m, 4H), 3.01(d, 2H,J=8.0 Hz), 4.25(d, 2H, J=6.4 Hz), 4.60(t, 1H,J=6.4 Hz), 4.98~5.18(m, 2H), 6.77(s, 1H), 6.98(s, 1H), 7.25(dd, 1H, J=2.1, 8.4 Hz), 7.29(s, 1H), 7.37(d, 1H, J=2.1 Hz), 7.42(d, 1H, J=8.4 Hz).

IR $\nu^{neat}$cm$^{-1}$: 2976, 2928, 2860, 1590, 1506, 1474, 1448, 1386, 1288, 1232, 1108, 1078, 1052, 866, 826, 784, 734, 662.

1.04 g of the thus obtained oil was dissolved in a proper amount of ethanol, and added fumaric acid (0.44 g) in ethanol. After removal of the ethanol, the residue was recrystallized from acetone-hexane. 0.72 g of fumarate of Compound 10 was obtained as white crystals.

EXAMPLE 11

Preparation of (Z)-1-(2,4-dichlorophenyl)-2-(1H-imidazole-1-yl)-O-((E)-3,7-dimethylocta-2,6-dienyl) ethanonoxime (Compound 11)

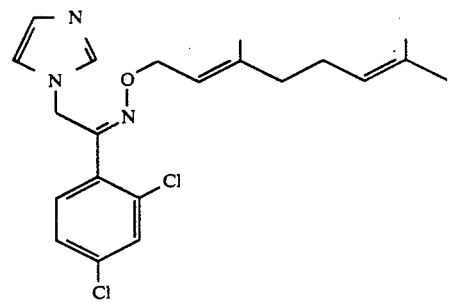

To a stirred suspension of (Z)-1-(2,4-dichlorophenyl)-2-(1H-imidazole-yl)ethanonhydroxime (2.00 g=7.4 mmol) in acetone (30 ml) was added crashed potassium hydroxide (0.38 g=6.7 mmol) at room temperature. Stirring continued for one hour and the reaction mixture was cooled to 0° C. (E)-3,7-dimethylocta-2,6-dienyl-1-bromide (1.47 g=7.4 mmol) was added dropwise to the mixture with stirring. The mixture was stirred for 30 minutes at room temperature, and 200 ml of saturated saline was added thereto. Extraction with ethyl acetate, drying (Na$_2$SO$_4$), and concentration followed by column chromatography on silica gel (ethyl acetate: hexane=2:3) gave 0.52 g of Compound 11 as a colorless oil.

$^1$H-NMR(CDCl$_3$) δ ppm: 1.62(s, 3H), 1.69(s, 3H), 1.74(s, 3H), 1.98~2.24(m, 4H), 4.77(d, 1H, J=6.9 Hz), 5.08~5.19(m, 1H), 5.20(s, 2H), 5.49(t, 1H, J=6.9 Hz), 6.76(s, 1H), 6.91(s, 1H), 7.00(d, 1H, J=8.2 Hz), 7.17(dd, 1H, J=8.2, 2.0 Hz), 7.37(s, 1H), 7.38(d, 1H, J=2.0 Hz).

IR $\nu^{neat}$cm$^{-1}$: 2968, 2926, 1590, 1506, 1479, 1446, 1383, 1233, 1107, 1077, 1005, 822.

What is claimed is:

1. An azole derivative represented by the formula (1):

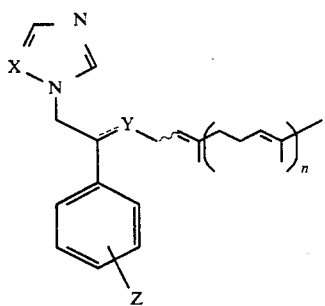

(I)

wherein X is a nitrogen atom, Y is an oxygen atom, a sulfur atom, an imino group, a methylimino group or a group represented by =N~O—, Z is one or two halogen atoms, n is 1 or 2, the wavy line indicates that the stereochemistry of the double bond is either E or Z; or an acid adduct thereof.

2. An antifungal composition comprising a therapeutically effective amount of the azole derivative of claim 1 or an acid adduct thereof and a pharmaceutically acceptable carrier.

* * * * *